(12) United States Patent
Brown et al.

(10) Patent No.: US 10,107,774 B2
(45) Date of Patent: Oct. 23, 2018

(54) OPTICALLY INTERFACED FUEL CHARACTERISTIC SENSOR

(71) Applicant: Simmonds Precision Products, Inc., Vergennes, VT (US)

(72) Inventors: Rollin W. Brown, South Burlington, VT (US); Robbie W. Hall, Charlotte, VT (US)

(73) Assignee: Simonds Precision Products, Inc., Vergennes, VT (US)

( * ) Notice: Subject to any disclaimer, the term of this patent is extended or adjusted under 35 U.S.C. 154(b) by 280 days.

(21) Appl. No.: 15/074,060

(22) Filed: Mar. 18, 2016

(65) Prior Publication Data
US 2017/0269018 A1    Sep. 21, 2017

(51) Int. Cl.
| | | |
|---|---|---|
| *G01F 17/00* | (2006.01) |
| *G01N 27/22* | (2006.01) |
| *G01K 7/16* | (2006.01) |
| *G01N 33/22* | (2006.01) |
| *H04B 10/80* | (2013.01) |
| *B64D 37/00* | (2006.01) |
| *G08C 23/06* | (2006.01) |
| *H04Q 9/00* | (2006.01) |
| *G01F 23/26* | (2006.01) |

(52) U.S. Cl.
CPC ........... *G01N 27/228* (2013.01); *B64D 37/00* (2013.01); *G01K 7/16* (2013.01); *G01N 33/22* (2013.01); *G08C 23/06* (2013.01); *H04B 10/807* (2013.01); *H04Q 9/00* (2013.01); *G01F 23/263* (2013.01); *H04Q 2209/886* (2013.01)

(58) Field of Classification Search
CPC .............................. G01N 27/228; G01N 33/22
USPC ........................................................... 702/52
See application file for complete search history.

(56) References Cited

U.S. PATENT DOCUMENTS

| | | | |
|---|---|---|---|
| 4,963,729 A | 10/1990 | Spillman et al. |
| 5,049,825 A | 9/1991 | Kline |
| 5,077,527 A | 12/1991 | Patriquin |
| 6,670,601 B1 | 12/2003 | Wyler |
| 6,744,036 B2 | 6/2004 | Kline |
| 7,259,384 B2 | 8/2007 | Hariram et al. |
| 7,965,948 B1 | 6/2011 | Bugash et al. |
| 2014/0166852 A1 | 6/2014 | Hauzeray |
| 2014/0331763 A1 | 11/2014 | Robb et al. |

OTHER PUBLICATIONS

Extended European Search report for EP Application No. 17157134.2, dated Aug. 29, 2017, 8 pages.

*Primary Examiner* — Anthony Ho
(74) *Attorney, Agent, or Firm* — Kinney & Lange, P.A.

(57) ABSTRACT

A sensor assembly includes a capacitive probe, a resistive element, an electronic circuit and an optical interface. A capacitance of the capacitive probe and a resistance of the resistive element are indicative of characteristics of an environment. The electronic circuit is configured to convert the capacitance and the resistance into optical data. The optical interface is configured to provide the optical data to an optical link.

14 Claims, 3 Drawing Sheets

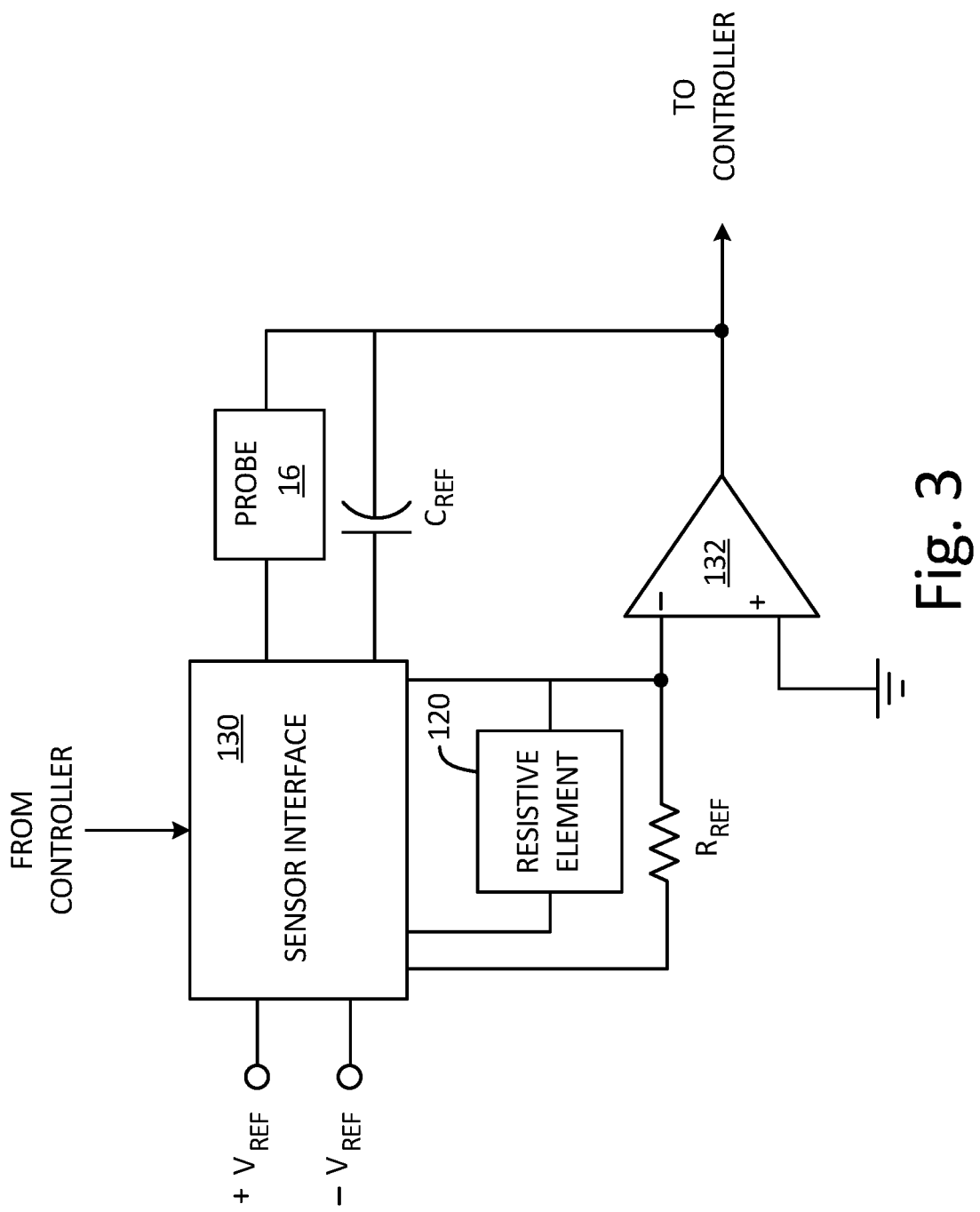

OPTICALLY INTERFACED FUEL CHARACTERISTIC SENSOR

BACKGROUND

The present invention relates generally to fluid sensors, and in particular to an optically interfaced fuel characteristic sensor assembly.

In fluid systems such as those on aircraft, for example, it is desirable to accurately determine properties related to the fluid, such as fluid height, fluid dielectric, fluid temperature and fluid conductivity. Increasingly stringent safety standards are required of these devices due to the inherently volatile environment and thus, the amount of energy permitted within a fuel tank, for example, is limited. Prior art fluid sensors included electrical interfaces connected to traditional copper wires. These electrical interfaces necessitated additional safety features in the design and implementation of the sensors to ensure that no arcing occurred and that other electrical energy within the fuel tank was limited. Therefore, it is desirable to eliminate the electrical interfaces from sensor assemblies while maintaining the same connectivity to external systems.

SUMMARY

A sensor assembly includes a capacitive probe, a resistive element, an electronic circuit and an optical interface. A capacitance of the capacitive probe and a resistance of the resistive element are indicative of characteristics of an environment. The electronic circuit is configured to convert the capacitance and the resistance into optical data. The optical interface is configured to provide the optical data to an optical link.

A method of sensing fluid characteristics within a fuel tank includes receiving, by an optical interface of a sensor assembly, optical energy from an optical link; powering sensor electronics using the optical energy; obtaining data, using sensing elements, indicative of the fluid characteristics within the fuel tank, wherein the sensing elements include a resistive element and a capacitive element; converting, using a controller, the data into optical data; and outputting the optical data, using the optical interface, on the optical link.

BRIEF DESCRIPTION OF THE DRAWINGS

FIG. 3 is a circuit diagram illustrating sensor interface electronics of an electronic assembly of a fuel characteristic sensor.

DETAILED DESCRIPTION

An optically interfaced fluid characteristic sensor is disclosed herein that includes resistive and/or capacitive sensing elements. The capacitive element may be utilized to determine a height of fluid within a tank, for example, and the resistive element may be utilized to determine the conductivity of the fluid and/or a temperature within the tank. A controller and integrator may be included within the sensor electronics to select between the resistive element and the capacitive element. The controller and integrator may be configured to control excitation to the resistive and capacitive elements, and to monitor the electrical response of the sensing elements to determine the characteristics of the fluid. The electrical response of the sensing elements may be converted into values indicative of properties of the fluid and transformed into optical output data for transmission on an optical link. The sensor electronics are powered using optical energy transmitted to the sensor on the optical link. The optical energy may be converted into electrical energy and stored for use by the sensor electronics.

Figure 1:
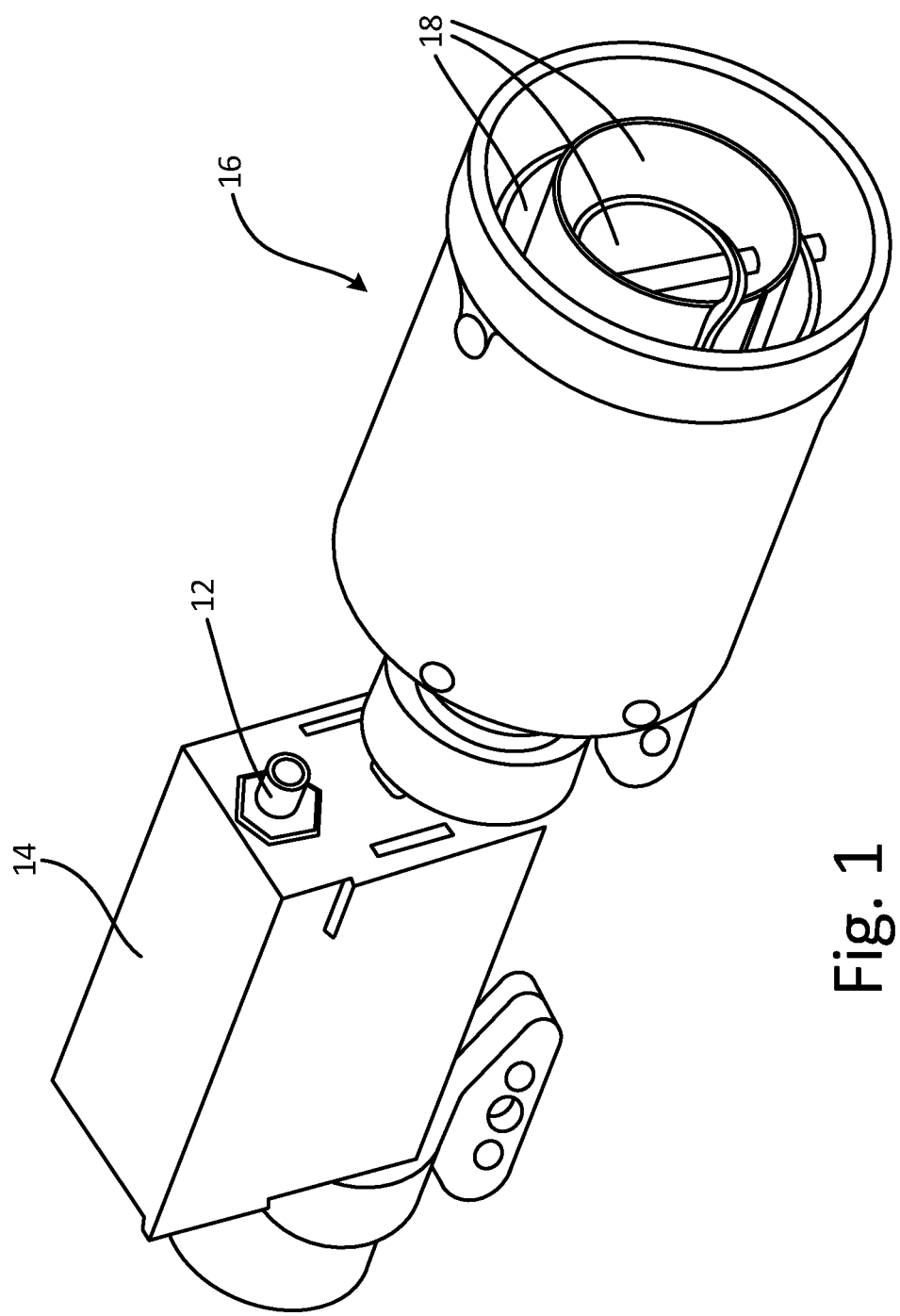
FIG. 1 is a diagram illustrating a fuel characteristic sensor assembly that includes an optical interface.

FIG. 1 is a diagram illustrating a fuel characteristic sensor assembly 10, which includes optical interface 12, electronics enclosure 14 and capacitive probe 16. Capacitive probe 16 may include concentric tubes 18 and may be configured for immersion within a fluid. For example, fuel characteristic sensor assembly 10 may be mounted within a fuel tank of an aircraft. An electronics assembly of fuel characteristic sensor assembly 10 may be housed within electronics enclosure 14, which may be any enclosure that is fluid-tight to prevent fuel from entering. In an embodiment, concentric tubes 18 may act as capacitor plates such that capacitive probe 16 acts as a variable capacitor depending on the height of the fluid within the plates. In other embodiments, other geometric configurations may be utilized for the variable capacitor. Although discussed as a fuel characteristic sensor assembly, sensor assembly 10 may be utilized to sense characteristics of any fluid.

Optical interface 12 may be configured to connect to an optical link, such as an optical fiber cable, for example. The optical link is configured to provide both power and data transmission for fuel characteristic sensor assembly 10. Power may be provided from, and data may be transmitted to, a remote system such as a fuel avionics systems, for example. Optical interface 12 may be the only external interface of electronics enclosure 14, providing an intrinsically safe enclosure for the electronic systems of assembly 10. This is advantageous in systems such as fuel tanks in which it is desirable to limit or eliminate the negative effects of lightning strikes, short circuits and/or other electrical threats that may compromise the safety of the environment.

Figure 2:
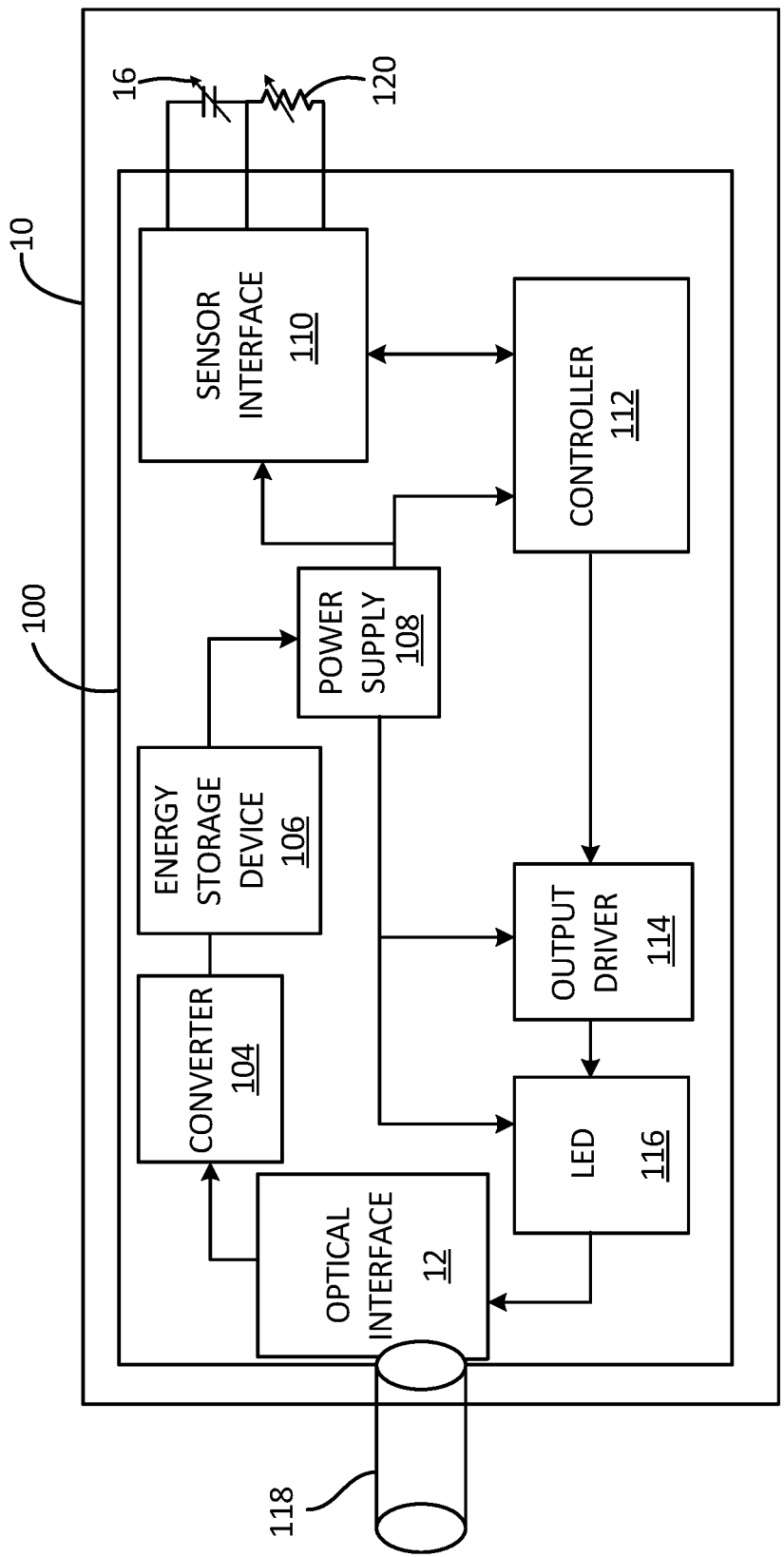
FIG. 2 is a block diagram illustrating the electronic assembly of a fuel characteristic sensor assembly that includes an optical interface.

FIG. 2 is a block diagram illustrating electronic assembly 100 of fuel characteristic sensor 10 that includes optical interface 12. Electronic assembly 100 may be housed in electronics enclosure 14 illustrated in FIG. 1. Electronic assembly 100 includes optical interface 12, optical power converter 104, energy storage device 106, power supply 108, sensor interface electronics 110, controller 112, output driver 114, and light-emitting diode (LED) 116. Optical interface 12 is connectable to optical link 118. Electronic assembly 100 is connected to capacitive probe 16 and/or resistive element 120. Resistive element 120 may be a resistance temperature detector (RTD) or any other element capable of providing information about the environment based upon a change in resistance of the device. While illustrated as an LED, LED 116 may be any other light source, such as a laser, capable of emitting light to optical link 118. Controller 112 may be implemented as any electronic circuit such as, for example, a digital signal processor (DSP) or other microprocessor, a field-programmable gate array (FPGA), or any other digital logic circuit. Sensor interface electronics 110 may include an integrator circuit, for example, that provides timing outputs indicative of measurements of capacitive probe 16 and/or resistive element 120. While illustrated with both capacitive probe 16 and resistive element 120, sensor assembly 10 may include only a capacitive probe 16 or only a resistive element 120.

Optical link 118 may be a single optical fiber cable, for example. Optical energy may be delivered to electronic assembly 100 on optical link 118 from a remote system. A fuel avionics system onboard an aircraft, for example, may be configured to provide optical energy over optical link 118 to fuel characteristic sensor assembly 10. Optical interface 12 directs the received optical energy to optical power converter 104. Optical power converter 104 may include one or more semiconductor devices, for example, that are capable of producing an electrical output based on the optical input. In an embodiment, several photodiodes may be connected in series to generate a desired output voltage from the optical input energy. The output voltage may be applied to energy storage device 106 for storage of the electrical energy. For example, a capacitor, or any other electrical storage device, may be connected across a plurality of photodiodes to store the electrical energy generated by the photodiodes. Power supply 108 may be configured to condition power from energy storage device 106 for the electronics of electronic assembly 100. For example, power supply 108 may include boost and/or buck circuits to step up or step down the voltage from energy storage device 106 based on the needs of the electronic components of electronic assembly 100.

Sensor interface electronics 110 may be configured to provide excitation to capacitive probe 16 (illustrated as a capacitor in FIG. 2) and resistive element 120. Sensor interface electronics 110 may also include a switching circuit to select between use of the resistive element 120 and the capacitive probe 16. Sensor interface electronics 110 may be implemented as a dual-slope integrator, for example. Dual slope integrators are analog-to-digital converters that are configured to determine unknown circuit characteristics based upon ramp-up and ramp-down times of an output voltage based on an input voltage. These dual-slope integrators may utilize resistor-capacitor (RC) circuits to facilitate the ramp-up and ramp-down functions. To determine the value of capacitance of capacitive probe 16, an RC circuit that includes capacitive probe 16 itself along with a reference resistor may be used by sensor interface electronics 110. To determine the value of resistance of resistive element 120, an RC circuit that includes a reference capacitor along with the resistive element may be utilized by sensor interface electronics 110.

Controller 112 may be configured to control the switching circuit of sensor interface electronics 110 to select between the resistive and capacitive sensing elements. Based on the selection, a value indicative of the resistance of resistive element 120 or of the capacitance of capacitive probe 16 may be provided to controller 112 from sensor interface electronics 110. Controller 112 may utilize the value to determine a respective property of the sensing element, or may simply relay the value from the integrator 110 onto optical link 118 for later determination by the remote system. In any situation, controller 112 conditions the output data for transmission onto optical link 118.

Data may be output from controller 112 as serial data, for example, or any other form of data suitable for transmission optical link 118. The data from controller 112 is provided to output driver 114, which conditions the data for conversion to optical data by LED 116. Output driver 114 drives LED 116 based upon the data from controller 112 such that the light produced by LED 116 is provided to optical link 118 and is representative of the data from controller 112. The optical data may be transmitted over optical link 118 to a remote system such as a fuel avionics system, for example, and may utilize any transmission protocol desired by the remote system.

FIG. 3 is a circuit diagram illustrating a portion of sensor interface electronics 110 of fuel characteristic sensor assembly 10 in an embodiment of sensor assembly 10 that includes both resistive element 120 and capacitive probe 16. Sensor interface 130, which may include a switching circuit, for example, is connected to reference resistor $R_{REF}$, reference capacitor $C_{REF}$, resistive element 120, capacitive probe 16 and operational amplifier (op-amp) 132. Sensor interface 130 may be configured to select between first and second signal paths, as well as select between input reference voltages ($+V_{REF}$ and $-V_{REF}$). The first and second signal paths make up resistor-capacitor (RC) circuits, for example, utilized to generate voltage ramps at the output of op-amp 132. Sensor interface 130 may be controlled by controller 12, for example, to select between the first and second signal paths. Sensor interface 130 may include a plurality of electrically controlled switches such as, for example, metal-oxide-semiconductor field-effect transistors (MOSFETs), insulated-gate bipolar transistors (IGBTs) or any other type of electronically controlled electrical or mechanical switches.

In an embodiment, sensor interface electronics 110 may include an integrator circuit, for example. With an integrator circuit, when $+V_{REF}$ is selected as input, the output of op-amp 132 has a positive slope (ramp-up) that increases from approximately zero to an upper value and when $-V_{REF}$ is selected as input, the output of op-amp 132 has a negative slope (ramp-down) that decreases from the upper value to approximately zero. The time periods of the ramp-up and ramp-down of the output of op-amp 132 is dependent upon the values of $V_{REF}$ and the selected integrator path. The first integrator path may form an RC circuit that includes reference resistor $R_{REF}$ and capacitive probe 16. For example, $+/-V_{REF}$ may be provided to resistor $R_{REF}$ through sensor interface 130. The output of resistor $R_{REF}$ may be connected to the inverting input of op-amp 132. Capacitive probe 16 may be connected between the output of resistor $R_{REF}$ and the output of op-amp 132 through sensor interface 130 to receive excitation. Knowing the values of $V_{REF}$ and $R_{REF}$, the time periods of the ramp-up and ramp-down of the output of op-amp 132 may be utilized to determine a value of the capacitance of capacitive probe 16. This determination may be done by controller 112 on sensor assembly 10, or the timing signals may be transmitted to a remote system which may perform the determination of the capacitance remotely.

The second integrator path may form an RC circuit that includes resistive element 120 and reference capacitor $C_{REF}$. For example, $+/-V_{REF}$ may be provided to excite resistive element 120 through sensor interface 130. The output of resistive element 120 may be connected to the inverting input of op-amp 132. Reference capacitor $C_{REF}$ may be connected between the output of resistive element 120 and the output of op-amp 132 through sensor interface 130. Knowing the values of $V_{REF}$ and $C_{REF}$, the time periods of the ramp-up and ramp-down of the output of op-amp 132 may be utilized to determine a value of the resistance of resistive element 120. This determination may be done by controller 112 on sensor assembly 10, or the timing signals may be transmitted to a remote system which may do the determination of the capacitance remotely. While illustrated using sensor interface 130, reference voltage $V_{REF}$, op-amp 132, reference capacitor $C_{REF}$ and reference resistor $R_{REF}$, sensor interface electronics 110 may be configured in any way that provides an output to controller 112 that is indicative of the capacitance of capacitive probe 16 and/or resistance of resistive element 120.

Discussion of Possible Embodiments

The following are non-exclusive descriptions of possible embodiments of the present invention.

A sensor assembly includes a capacitive probe, a resistive element, an electronic circuit and an optical interface. A capacitance of the capacitive probe and a resistance of the resistive element are indicative of characteristics of an environment. The electronic circuit is configured to convert the capacitance and the resistance into optical data. The optical interface is configured to provide the optical data to an optical link.

The sensor assembly of the preceding paragraph can optionally include, additionally and/or alternatively, any one or more of the following features, configurations, operations, and/or additional components:

A further embodiment of the foregoing sensor assembly, wherein the optical interface is further configured to receive optical energy from the optical link, and wherein the sensor assembly further includes an optical power converter configured to convert optical energy from the optical link into electrical energy to power the sensor assembly.

A further embodiment of any of the foregoing sensor assemblies, further including an energy storage device configured to store the electrical energy from the optical power converter and to provide stored energy to the electronic circuit.

A further embodiment of any of the foregoing sensor assemblies, wherein the capacitive probe comprises two concentric tubes configured to be immersed within a fluid, and wherein the capacitance is indicative of a height of the fluid.

A further embodiment of any of the foregoing sensor assemblies, wherein the environment is an aircraft fuel tank, and wherein the fluid is fuel within the aircraft fuel tank.

A further embodiment of any of the foregoing sensor assemblies, wherein the electronic circuit includes a sensor interface circuit configured to provide timing outputs indicative of the capacitance and the resistance, and a controller configured to control the sensor interface circuit to select between the capacitive probe and the resistive element, and to convert the timing signals into the optical data.

A further embodiment of any of the foregoing sensor assemblies, wherein the sensor interface includes a first signal path configured to excite the capacitive probe, and a second signal path configured to excite the resistive element. The sensor interface circuit is configured to select between the first signal path and the second signal path.

A further embodiment of any of the foregoing sensor assemblies, wherein the controller is configured to control the sensor interface circuit to select between the first and second signal paths, and wherein the timing signals are indicative of the capacitance when the first signal path is selected, and wherein the timing signals are indicative of the resistance when the second signal path is selected.

A further embodiment of any of the foregoing sensor assemblies, wherein the optical link comprises a single optical fiber cable, and wherein both the optical data and the optical energy are transmitted on the single optical fiber cable.

A method of sensing fluid characteristics within a fuel tank includes receiving, by an optical interface of a sensor assembly, optical energy from an optical link; powering sensor electronics using the optical energy; obtaining data, using sensing elements, indicative of the fluid characteristics within the fuel tank, wherein the sensing elements include a resistive element and a capacitive element; converting, using a controller, the data into optical data; and outputting the optical data, using the optical interface, on the optical link.

The method of the preceding paragraph can optionally include, additionally and/or alternatively, any one or more of the following features, configurations, operations, and/or additional components:

A further embodiment of the foregoing method, wherein powering the sensor electronics using the optical energy includes converting, using a power convertor of the sensor assembly, the optical energy into electrical energy; and powering the sensor electronics using the electrical energy.

A further embodiment of any of the foregoing methods, wherein powering the sensor electronics using the electrical energy includes storing the electrical energy using an energy storage device; and distributing stored energy of the energy storage device to the sensor electronics.

A further embodiment of any of the foregoing methods, wherein obtaining data using the sensing elements includes converting analog data from the sensing elements into digital data using a sensor interface circuit; and providing the digital data to the controller.

A further embodiment of any of the foregoing methods, wherein the optical link comprises a single optical fiber cable.

A further embodiment of any of the foregoing methods, wherein the capacitive element is a capacitive probe comprising at least two concentric tubes configured to act as a variable capacitor.

A further embodiment of any of the foregoing methods, wherein the resistive element is a resistance temperature detector.

While the invention has been described with reference to an exemplary embodiment(s), it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed, but that the invention will include all embodiments falling within the scope of the appended claims.

The invention claimed is:
1. A sensor assembly comprising:
   a capacitive probe;
   a resistive element, wherein a capacitance of the capacitive probe and a resistance of the resistive element are indicative of characteristics of an environment;
   an electronic circuit configured to convert the capacitance and the resistance into optical data, wherein the electronic circuit comprises:
      a sensor interface circuit configured to provide timing outputs indicative of the capacitance and the resistance, wherein the sensor interface circuit comprises:
         a first signal path configured to excite the capacitive probe; and
         a second signal path configured to excite the resistive element;
         wherein the sensor interface circuit is configured to select between the first signal path and the second signal path; and
      a controller configured to control the sensor interface circuit to select between the first signal path and the second signal path, and to convert the timing signals into the optical data; and an optical interface configured to provide the optical data to an optical link.

2. The sensor assembly of claim 1, wherein the optical interface is further configured to receive optical energy from the optical link, and wherein the sensor assembly further comprises:
   an optical power converter configured to convert optical energy from the optical link into electrical energy to power the sensor assembly.

3. The sensor assembly of claim 2, further comprising an energy storage device configured to store the electrical energy from the optical power converter and to provide stored energy to the electronic circuit.

4. The sensor assembly of claim 3, wherein the capacitive probe comprises two concentric tubes configured to be immersed within a fluid, and wherein the capacitance is indicative of a height of the fluid.

5. The sensor assembly of claim 4, wherein the environment is an aircraft fuel tank, and wherein the fluid is fuel within the aircraft fuel tank.

6. The sensor assembly of claim 1, wherein the controller is configured to control the sensor interface circuit to select between the first and second signal paths, and wherein the timing signals are indicative of the capacitance when the first signal path is selected, and wherein the timing signals are indicative of the resistance when the second signal path is selected.

7. The sensor assembly of claim 2, wherein the optical link comprises a single optical fiber cable, and wherein both the optical data and the optical energy are transmitted on the single optical fiber cable.

8. A method of sensing fluid characteristics within a fuel tank, the method comprising:
   receiving, by an optical interface of a sensor assembly, optical energy from an optical link;
   powering sensor electronics using the optical energy, wherein the sensor electronics include a first signal path and a second signal path;
   selecting, by a controller, between the first signal path and the second signal path;
   outputting, by a sensor interface circuit, timing signals as data indicative of the fluid characteristics within the fuel tank, wherein the sensing elements include a resistive element and a capacitive element, and wherein the first signal path includes the capacitive element and a reference resistor, and wherein the second signal path includes the resistive element and a reference capacitor;
   converting, using the controller, the data into optical data; and
   outputting the optical data, using the optical interface, on the optical link.

9. The method of claim 8, wherein powering the sensor electronics using the optical energy comprises:
   converting, using a power convertor of the sensor assembly, the optical energy into electrical energy; and
   powering the sensor electronics using the electrical energy.

10. The method of claim 9, wherein powering the sensor electronics using the electrical energy comprises:
    storing the electrical energy using an energy storage device; and
    distributing stored energy of the energy storage device to the sensor electronics.

11. The method of claim 8, wherein converting, using the controller, the data into the optical data comprises:
    converting analog data from the sensing elements into digital data using a sensor interface circuit; and
    providing the digital data to the controller.

12. The method of claim 8, wherein the optical link comprises a single optical fiber cable.

13. The method of claim 8, wherein the capacitive element is a capacitive probe comprising at least two concentric tubes configured to act as a variable capacitor.

14. The method of claim 13, wherein the resistive element is a resistance temperature detector.

* * * * *